United States Patent [19]
Green

[11] 4,282,353
[45] Aug. 4, 1981

[54] PROCESS FOR THE PREPARATION OF UNSATURATED KETONES CONTAINING GLYCIDYL GROUPS

[75] Inventor: George E. Green, Stapleford, England

[73] Assignee: Ciba-Geigy Corporation, Ardsley, N.Y.

[21] Appl. No.: 95,873

[22] Filed: Nov. 19, 1979

[30] Foreign Application Priority Data

Nov. 30, 1978 [GB] United Kingdom ............... 46657/78

[51] Int. Cl.$^3$ .......................................... C07D 301/00
[52] U.S. Cl. .............................. 542/438; 260/348.42; 260/348.43; 260/348.45; 260/348.49; 260/348.58; 260/348.63; 260/348.64
[58] Field of Search ...................... 542/413, 420, 438; 260/348.58, 348.64

[56] References Cited

U.S. PATENT DOCUMENTS

| | | | |
|---|---|---|---|
| 3,012,044 | 12/1961 | Hudson | 260/348.56 |
| 3,937,685 | 2/1976 | Kolbel et al. | 260/348.64 |

OTHER PUBLICATIONS

Noller, Chemistry of Organic Compounds, 2nd ed., p. 536, W. B. Saunders Co., Philadelphia, USA (1957).
Gould, Mechanism and Structure in Organic Chemistry, frontispage and p. 389, Holt, Rinehart and Winston, NY (1959).
Lee et al., Handbook of Epoxy Resins, frontispage and p. 5-12, McGraw—Hill Book Co. (NY).

*Primary Examiner*—John D. Randolph
*Attorney, Agent, or Firm*—Luther A. R. Hall

[57] ABSTRACT

Diglycidyl unsaturated ketones of formula

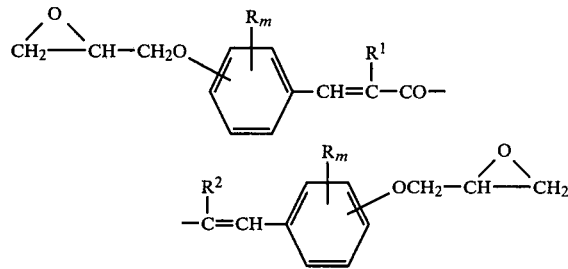

e.g., 1,5-bis(p-glycidyloxyphenyl)-1,4-pentadien-3-one, are prepared by condensing one molar equivalent of a ketone of formula

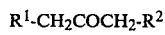

$R^1$-$CH_2COCH_2$-$R^2$ with two molar equivalents of an o- or p- glycidyloxybenzaldehyde of formula

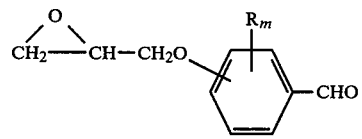

in the presence of a basic catalyst, where
R represents an alkyl or alkoxy group of 1 to 5 carbon atoms, an alkenyl group of 2 to 5 carbon atoms, a carbalkoxy group of 2 to 10 carbon atoms, a cycloalkyl group of 5 to 8 carbon atoms, a halogen atom, a nitro group, or a carboxyl, sulfonic acid, or phosphonic acid group in the form of a salt,
m represents zero or 1 to 4, and
$R^1$ and $R^2$ each represent a hydrogen atom or an alkyl group of 1 to 5 carbon atoms, or together form a straight chain or branched alkylene group of 2 to 6 carbon atoms.

The products are useful as photopolymerizable resins.

9 Claims, No Drawings

PROCESS FOR THE PREPARATION OF UNSATURATED KETONES CONTAINING GLYCIDYL GROUPS

BACKGROUND OF THE INVENTION

This invention relates to a process for the preparation of unsaturated ketones containing two glycidyloxy groups directly attached to carbon atoms of aromatic rings, and to such ketones prepared by the new process.

Certain ethylenically unsaturated ketones containing two glycidyloxy groups directly attached to carbon atoms of aromatic rings are known to be light-sensitive and have been used in the photochemical production of printing plates and printed circuits. Their preparation and use have been described in, for example, British Pat. No. 1,076,650 and U.S. Pat. No. 3,937,685.

These ketonic glycidyl ethers have been prepared by reaction of an unsaturated ketone having two phenolic hydroxyl groups with an excess of epichlorohydrin, usually under alkaline conditions. The unsaturated ketone having two phenolic hydroxyl groups has itself been prepared by reaction of two molar equivalents of a phenolic aldehyde with one molar equivalent of a ketone containing two active methylene groups, usually acetone. This process suffers from a serious disadvantage when carried out commercially. It has been found that, in order to obtain satisfactory yields, the reaction between the aldehyde and the ketone must be conducted in the presence of a large excess of an acid, gaseous hydrogen chloride usually being employed. This acid causes extensive corrosion when used on an industrial scale unless costly precautions precautions are taken. Further, extreme care is required in handling this acid.

It has now been found that the preparation of unsaturated ketones containing two O-glycidyl groups directly attached to aromatic rings may be effected entirely in the presence of an alkaline catalyst whilst still obtaining the good yields usually associated with acid catalysts. Further, the product has the high degree of purity necessary for its use in photopolymerisation applications. In this new method 2 molar equivalents of an o- or p-glycidyloxybenzaldehyde are condensed with one molar equivalent of a ketone containing two active methylene groups.

DETAILED DISCLOSURE

Accordingly, this invention comprises a process for the preparation of diglycidyl unsaturated ketones of the general formula

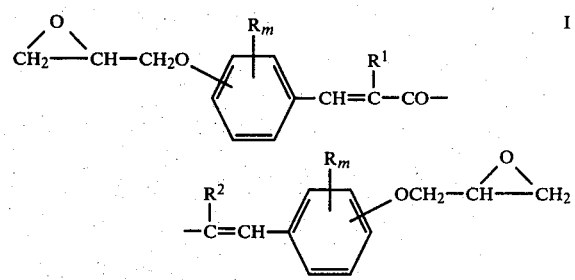

each glycidyloxy group being ortho or para to the group

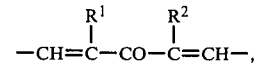

which comprises condensation of one molar equivalent of a ketone of formula $$R^1-CH_2COCH_2-R^2 \quad \text{II}$$

with two molar equivalents of a glycidyloxybenzaldehyde of formula

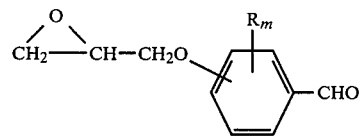

the glycidyloxy group whereof being ortho or para to the aldehyde group, in the presence of a basic catalyst, where R represents a straight chain or branched alkyl or alkoxy group having from 1 to 5 carbon atoms, an alkenyl group having from 2 to 5 carbon atoms, a carbalkoxy group having from 2 to 10 carbon atoms, a cycloalkyl group having from 5 to 8 carbon atoms, a halogen atom, a nitro group, or a carboxyl, sulfonic acid, or phosphonic acid group in the form of a salt, m represents zero or a positive integer of from 1 to 4, and when m is greater than 1 the groups represented by R on the same aromatic ring may be the same or different, and $R^1$ and $R^2$, which may be the same or different, each represents a hydrogen atom or an alkyl group of from 1 to 5 carbon atoms, or $R^1$ and $R^2$ together form a straight chain or branched alkylene group of from 2 to 6 carbon atoms.

This invention further comprises diglycidyl unsaturated ketones of formula I prepared by the new process.

The basic catalyst used in the new process may be any base. Typically, it is an alkali metal carbonate, alkoxide, or hydroxide, sodium and potassium hydroxides being particularly preferred. Usually, 0.1 to 2 equivalents of base are employed per mole of aldehyde of formula III, more particularly 0.25 to 1 equivalent. It is especially preferred to use 0.4 to 0.6 equivalent of base per mole of aldehyde of formula III.

The reaction may be effected in the absence of a solvent, but is preferably effected in an inert solvent, such as an ether, a hydrocarbon or, more especially, an alkanol containing at most 5 carbon atoms, such as methanol or ethanol. These alkanols may be used alone or in admixture with water. The temperature of the reaction is not critical and condensation may take place at −20° C. or at any temperature up to the boiling point of the reaction mixture. Temperatures within the range 0° to 50° C. are preferred.

Preferred compounds prepared by the process of the present invention are those where, in formula I, $R^1$ and $R^2$ both represent a hydrogen atom or together form a 2-methylpropylene (—CH$_2$CH(CH$_3$)CH$_2$—, trimethylene, or ethylene chain, and those where m represents zero, or where m represents 1 and R represents an alkoxy group, are further preferred.

The o- and p-glycidyloxybenzaldehydes of formula III used as starting materials in the novel process, are, in general, known compounds, and have been described in, for example, U.S. Pat. No. 3,012,044 and Weissermel, Fischer, Haefner, and Cherdron, *Angew. Makromol. Chem.*, 1968, 4/5, 168–184. They may be prepared by the reaction, under alkaline conditions, of a hydroxybenzaldehyde of the formula

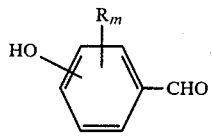

where R and m are as hereinbefore defined and the hydroxy group is ortho or para to the aldehyde group, with an excess, on a molar basis, of epichlorohydrin, followed by dechlorination.

The invention will now be illustrated by the following Examples, in which all parts and percentages are by weight.

Epoxide contents of p-glycidyloxybenzaldehyde and its analogues were determined by titration against a 0.1 N solution of perchloric acid in glacial acetic acid in the presence of an excess of tetraethyl ammonium bromide, crystal violet being used as the indicator.

Epoxide contents of the condensation products were determined by potentiometric titration against 0.1 N perchloric acid in glacial acetic acid in the presence of tetraethylammonium bromide, using glass and lithium chloride electrodes.

p-Glycidyloxybenzaldehyde, used as starting material, was prepared by either of the following methods:

Method A

This method is similar to that described in U.S. Pat. No. 3,012,044 but with minor modifications.

A solution of p-hydroxybenzaldehyde (122 g; 1 mole) in 800 ml of 1.25 N aqueous sodium hydroxide (40 g; 1 mole) was added over 2½ hours to 278 g of epichlorohydrin (3 moles) stirred at 60° C. The reaction mixture was stirred for a further 30 minutes at 60° C. after the addition was complete, then allowed to cool to room temperature and the product was extracted into 200 ml of dichloromethane. The organic phase was washed with 200 ml of 0.5 N aqueous sodium hydroxide solution, then with 200 ml of 10% aqueous sodium dihydrogen orthophosphate solution, and finally twice with 200 ml of water. The organic phase was then dried over magnesium sulphate and the solvent was removed under reduced pressure. The product had an epoxide content of 4.9 equivalents/kg (theoretical epoxide content 5.62 equivalents/kg). Yield 90%.

Distillation of this material (122°–130° C./0.7 mm) gave a product having an epoxide content of 5.49 equivalents/kg, which crystallised on standing (m.p. 37° C.).

Method B

An alternative preparation of this material, which affords higher initial epoxide contents and eliminates the need for distillation, is as follows:

A solution of sodium hydroxide (44 g; 1.1 moles) in water (500 ml) was added over 2½ hours to a solution of p-hydroxybenzaldehyde (122 g; 1 mole) in 278 g of epichlorohydrin (3 moles) stirred at 60° C. The mixture was stirred for a further 30 minutes at 60° C. after the addition was complete. The reaction mixture was allowed to cool to room temperature and the product was extracted and washed as described in Method A.

A 95% yield of product was obtained which an epoxide content of 5.25 equivalents/kg.

Vanillin glycidyl ether (3-methoxy-4-glycidyloxybenzaldehyde) was prepared in a similar manner to Method A, but starting from vanillin in place of p-hydroxybenzaldehyde. The yield was 96% of theory, the product having an epoxide content of 4.41 equivalents/kg (theoretical value 4.8 equivalents/kg). A sample was recrystallised from ethanol, giving 95% recovery of product having an epoxide content of 4.76 equivalents/kg, melting point 101° C. Salicylaldehyde glycidyl ether (o-glycidyloxybenzaldehyde) may be prepared in a like manner from salicylaldehyde.

EXAMPLE I p-Glycidyloxybenzaldehyde (80 g; prepared according to Method B) in acetone (13 g) and ethanol (80 g) was added over 1 hour to a stirred solution of sodium hydroxide (9 g) in a mixture of water (90 g) and ethanol (80 g), keeping the temperature at 25° to 30° C. On complete addition the mixture was stirred at 25° to 30° C. for a further hour, then filtered. The residue was dissolved in epichlorohydrin (400 ml), washed at 60° C. with 5% aqueous sodium hydrogen sulfate (100 ml), then with water (200 ml). The solution was dried over anhydrous magnesium sulfate and evaporated under reduced pressure to give 1,5-bis(p-glycidyloxyphenyl)-1,4-pentadien-3-one. The yield was 58 g (68% of theoretical yield) and the product had an epoxide content of 4.5 equivalents/kg (theoretical value 5.29 equivalents/kg). On recrystallisation from ethanol the epoxide content of the product was 5.18 equivalents/kg. This product was shown to be identical with an authentic sample of 1,5-bis(p-glycidyloxyphenyl)-1,4-pentadien-3-one by gel permeation chromatography and by NMR, UV, and IR spectral analysis.

In a similar manner, but replacing the p-glycidyloxybenzaldehyde by 2,6-dimethyl-4-glycidyloxybenzaldehyde or 3-allyl-4-glycidyloxybenzaldehyde, there may be obtained 1,5-bis(2,6-dimethyl-4-glycidyloxyphenyl)-1,4-pentadien-3-one or 1,5-bis(3-allyl-4-glycidyloxyphenyl)-1,4-pentadien-3-one.

EXAMPLE 2

Distilled p-glycidyloxybenzaldehyde (40 g; prepared according to Method A) in acetone (6.5 g) and ethanol (40 g) was added over 1 hour to a stirred solution of sodium hydroxide (4.5 g) in a mixture of water (45 g) and ethanol (40 g), keeping the temperature at 25° to 30° C. The mixture was then stirred at 25° to 30° C. for a further hour and filtered. The residue was washed with water, then with ethanol, and dried at 60° C. in vacuo to give 1,5-bis(p-glycidyloxyphenyl)-1,4-pentadien-3-one. The yield was 26.7 g (63% of theoretical yield) and the product had an epoxide content of 4.78 equivalents/kg.

This product was also shown to be identical with an authentic sample of 1,5-bis(p-glycidyloxyphenyl)-1,4-pentadien-3-one by gel permeation chromatography and by NMR, UV, and IR spectral analysis.

EXAMPLE 3

Vanillin glycidyl ether (5 g), dissolved in acetone (0.7 g) and methanol (40 g), was added over 1 hour to a stirred solution of sodium hydroxide (0.48 g) in a mixture of water (5 g) and methanol (5 g), keeping the temperature at 25° to 30° C. The mixture was left at room temperature overnight, then filtered. The residue was washed with water and ethanol, and dried at 60° C.

in vacuo to give 1,5-bis(3-methoxy-4-glycidyloxy-phenyl)-1,4-pentadien-3-one (epoxide content 2.34 equivalents/kg). This product was shown to be identical with an authentic sample of 1,5-bis(3-methoxy-4-glycidyloxyphenyl)-1,4-pentadien-3-one by examination of NMR spectra.

In a similar manner, but replacing the vanillin glycidyl ether by 2-methoxy-4-glycidyloxybenzaldehyde or o-glycidyloxybenzaldehyde, there may be obtained 1,5-bis(2-methoxy-4-glycidyloxyphenyl)-1,4-pentadien-3-one or 1,5-bis(o-glycidyloxyphenyl)-1,4-pentadien-3-one.

EXAMPLE 4

A solution of p-glycidyloxybenzaldehyde (40 g; prepared according to Method A) and cyclopentanone (9.4 g) in ethanol (40 g) was added over 1 hour to a stirred solution of sodium hydroxide (2.25 g) in a mixture of water (45 g) and ethanol (40 g), keeping the temperature at 25° to 30° C. On complete addition the mixture was stirred at 25° to 30° C. for a further 30 minutes, then water (100 g) was added and the mixture was stirred for 15 minutes. The precipitate was filtered off, washed with water and ice-cold ethanol, and dried at 60° C. in vacuo to give 1,3-bis(p-glycidyloxyphenylmethylidene)cyclopentan-2-one. The yield was 40 g (88% of theory) and the product had an epoxide content of 4.43 equivalents per kilogram, the theoretical value being 4.95 equivalents per kilogram. The N.M.R., I.R., and UV spectra of the product were consistent with the above structure.

In a similar manner, but replacing the cyclopentanone by cyclohexanone, cycloheptanone, or 4-methylcyclohexanone, there may be prepared 1,3-bis(p-glycidyloxyphenylmethylidene)cyclohexan-2-one, 1,3-bis(p-glycidyloxyphenylmethylidene)cycloheptan-2-one, or 1,3-bis(p-glycidyloxyphenylmethylidene)-4-methylcyclohexan-2-one.

I claim:

1. Process for the preparation of diglycidyl unsaturated ketones, in high yield and purity of the general formula

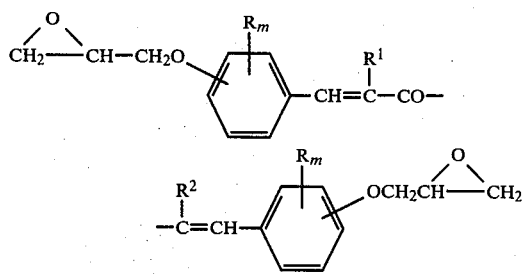  I which comprises condensation of one molar equivalent of a ketone of formula

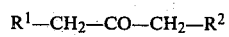  II with two molar equivalents of a glycidyloxybenzaldehyde of formula

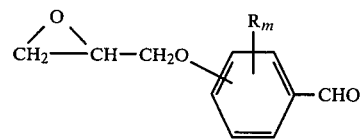  III in the presence of a basic catalyst, where
R represents a straight chain or branched alkyl or alkoxy group having from 1 to 5 carbon atoms, an alkenyl group having from 2 to 5 carbon atoms, a carbalkoxy group having from 2 to 10 carbon atoms, a cycloalkyl group having from 5 to 8 carbon atoms, a halogen atom, a nitro group, or a carboxyl, sulfonic acid, or phosphonic acid group in the form of a salt,
m represents zero or a positive integer of from 1 to 4, and when m is greater than 1 the groups represented by R on the same aromatic ring may be the same or different, and
$R^1$ and $R^2$, which may be the same or different, separately represent a hydrogen atom or an alkyl group of from 1 to 5 carbon atoms, or $R^1$ and $R^2$ together form a straight chain or branched alkylene group of from 2 to 6 carbon atoms,
each glycidyloxy group in formula I being ortho- or para- to the group

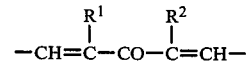

and the glycidyloxy group in formula III being ortho or para- to the aldehyde group.

2. The process of claim 1, wherein $R^1$ and $R^2$ both represent a hydrogen atom or together form a 2-methylpropylene, trimethylene, or ethylene chain.

3. The process of claim 1, wherein m represents either zero, or 1, in which case R represents a said alkoxy group.

4. The process of claim 1, in which the basic catalyst is an alkali metal carbonate, an alkali metal alkoxide, or an alkali metal hydroxide.

5. The process of claim 4, in which the basic catalyst is sodium hydroxide or potassium hydroxide.

6. The process of claim 1, in which there is used from 0.1 to 2 equivalents of base per mole of the aldehyde of formula III.

7. The process of claim 1, which is effected in the presence of an inert solvent.

8. The process of claim 7, in which the solvent is an alkanol of at most 5 carbon atoms, alone or in admixture with water.

9. The process of claim 1, carried out at a temperature within the range 0° to 50° C.

* * * * *